US009963556B2

(12) United States Patent
Huffstetler et al.

(10) Patent No.: US 9,963,556 B2
(45) Date of Patent: May 8, 2018

(54) CRITICAL POINT DRYING OF HYDROGELS IN ANALYTE SENSORS

(71) Applicant: Senseonics, Incorporated, Germantown, MD (US)

(72) Inventors: Philip Huffstetler, Germantown, MD (US); Aneta Modzelewska, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days. days.

(21) Appl. No.: 14/489,728

(22) Filed: Sep. 18, 2014

(65) Prior Publication Data

US 2015/0079669 A1 Mar. 19, 2015

Related U.S. Application Data

(60) Provisional application No. 61/879,475, filed on Sep. 18, 2013.

(51) Int. Cl.
| | |
|---|---|
| *C08J 3/00* | (2006.01) |
| *A61B 5/00* | (2006.01) |
| *A61B 5/1455* | (2006.01) |
| *A61B 5/1459* | (2006.01) |
| *G01N 21/64* | (2006.01) |
| *F26B 21/14* | (2006.01) |
| *A61B 5/145* | (2006.01) |

(52) U.S. Cl.
CPC ............... *C08J 3/00* (2013.01); *A61B 5/1455* (2013.01); *A61B 5/1459* (2013.01); *A61B 5/6861* (2013.01); *A61B 5/0071* (2013.01); *A61B 5/14532* (2013.01); *F26B 21/14* (2013.01); *G01N 21/6428* (2013.01)

(58) Field of Classification Search
CPC ........ C08J 3/00; A61B 5/1455; A61B 5/6861; A61B 5/1459; A61B 5/0071; A61B 5/14532; F26B 21/14; G01N 21/6428
See application file for complete search history.

(56) References Cited

U.S. PATENT DOCUMENTS

| | | | |
|---|---|---|---|
| 4,667,417 A | * | 5/1987 | Graser ............... B01D 11/0203 34/337 |
| 5,517,313 A | | 5/1996 | Colvin, Jr. |
| 5,772,864 A | | 6/1998 | Moller et al. |
| 5,833,603 A | | 11/1998 | Kovacs et al. |

(Continued)

FOREIGN PATENT DOCUMENTS

| | | |
|---|---|---|
| JP | S63-291595 A | 11/1988 |
| JP | 2001-513350 A | 9/2001 |

(Continued)

OTHER PUBLICATIONS

PCT International Search Report, issued in PCT/US2012/029209 dated Jun. 8, 2012, 17 pages.

(Continued)

*Primary Examiner* — Lore R Jarrett
(74) *Attorney, Agent, or Firm* — Rothwell, Figg, Ernst & Manbeck, P.C.

(57) ABSTRACT

A hydrogel is dried by a critical point drying technique. The hydrogel may include indicator molecules embedded therein and may be part of a hydrogel-based device, such as, for example, an analyte sensor.

5 Claims, 6 Drawing Sheets

(56) References Cited

U.S. PATENT DOCUMENTS

| | | | |
|---|---|---|---|
| 5,894,351 A | 4/1999 | Colvin, Jr. | |
| 5,910,661 A | 6/1999 | Colvin, Jr. | |
| 5,917,605 A | 6/1999 | Colvin, Jr. | |
| 5,922,183 A | 7/1999 | Rauh | |
| 6,189,536 B1 | 2/2001 | Martinez et al. | |
| 6,304,766 B1 | 10/2001 | Colvin, Jr. | |
| 6,330,464 B1 | 12/2001 | Colvin, Jr. et al. | |
| 6,344,360 B1 | 2/2002 | Colvin et al. | |
| 6,400,974 B1 | 6/2002 | Lesho | |
| 6,584,335 B1 | 6/2003 | Haar et al. | |
| 6,709,379 B1 | 3/2004 | Brandau et al. | |
| 6,794,195 B2 | 9/2004 | Colvin, Jr. | |
| 6,800,451 B2 | 10/2004 | Daniloff et al. | |
| 6,940,590 B2 | 9/2005 | Colvin, Jr. et al. | |
| 7,135,342 B2 | 11/2006 | Colvin, Jr. et al. | |
| 7,157,723 B2 | 1/2007 | Colvin et al. | |
| 7,190,445 B2 | 3/2007 | Colvin, Jr. et al. | |
| 7,308,292 B2 | 12/2007 | Colvin et al. | |
| 7,375,347 B2 | 5/2008 | Colvin, Jr. et al. | |
| 7,553,280 B2 | 6/2009 | Lesho | |
| 7,713,745 B2 | 5/2010 | Colvin, Jr. et al. | |
| 7,783,333 B2 | 8/2010 | Brister et al. | |
| 7,800,078 B2 | 9/2010 | Colvin, Jr. et al. | |
| 7,851,225 B2 | 12/2010 | Colvin, Jr. et al. | |
| 7,939,832 B2 | 5/2011 | Colvin et al. | |
| 8,073,548 B2 | 12/2011 | Colvin, Jr. et al. | |
| 8,143,068 B2 | 3/2012 | Colvin, Jr. et al. | |
| 8,233,953 B2 | 7/2012 | Colvin, Jr. | |
| 8,415,184 B2 | 4/2013 | Colvin et al. | |
| 8,923,947 B2 | 12/2014 | Shults et al. | |
| 2002/0176880 A1* | 11/2002 | Cruise | A61K 9/0024 424/423 |
| 2004/0063167 A1 | 4/2004 | Kaastrup et al. | |
| 2004/0091603 A1* | 5/2004 | Priewe | A61L 31/06 427/2.24 |
| 2004/0247674 A1* | 12/2004 | Haapakumpu | A61K 9/0024 424/471 |
| 2005/0074602 A1* | 4/2005 | Bjursten | A61L 27/306 428/334 |
| 2005/0095174 A1 | 5/2005 | Wolf | |
| 2005/0096587 A1 | 5/2005 | Santini, Jr. et al. | |
| 2005/0221277 A1 | 10/2005 | Kawanishi | |
| 2005/0227242 A1 | 10/2005 | Colvin, Jr. et al. | |
| 2005/0234616 A1 | 10/2005 | Colvin, Jr. et al. | |
| 2006/0076237 A1* | 4/2006 | Pluskal | B01D 57/02 204/450 |
| 2006/0129050 A1 | 6/2006 | Martinson et al. | |
| 2006/0270922 A1 | 11/2006 | Brauker et al. | |
| 2006/0282042 A1 | 12/2006 | Walters et al. | |
| 2007/0014726 A1 | 1/2007 | Merical et al. | |
| 2007/0027384 A1 | 2/2007 | Brister et al. | |
| 2007/0114138 A1 | 5/2007 | Krasteva et al. | |
| 2007/0191701 A1 | 8/2007 | Feldman et al. | |
| 2008/0125838 A1 | 5/2008 | Francis | |
| 2008/0228051 A1 | 9/2008 | Shults et al. | |
| 2009/0264718 A1 | 10/2009 | Lesho | |
| 2010/0024526 A1 | 2/2010 | Colvin, Jr. et al. | |
| 2010/0202966 A1 | 8/2010 | Gross et al. | |
| 2010/0298674 A1 | 11/2010 | Colvin, Jr. et al. | |
| 2011/0236989 A1 | 9/2011 | Suri et al. | |
| 2011/0255255 A1 | 10/2011 | Colvin et al. | |
| 2012/0053427 A1 | 3/2012 | Markle et al. | |
| 2012/0238842 A1 | 9/2012 | Colvin, Jr. et al. | |
| 2013/0052660 A1* | 2/2013 | Lee | G01N 21/6428 435/7.8 |
| 2013/0211213 A1 | 8/2013 | DeHennis et al. | |

FOREIGN PATENT DOCUMENTS

| | | |
|---|---|---|
| JP | 2002-523774 A | 7/2002 |
| JP | 2005-315871 A | 11/2005 |
| JP | 2007-532901 A | 11/2007 |
| JP | 2008-506469 A | 3/2008 |
| TW | 200838985 A | 10/2008 |
| TW | 201041612 A | 12/2010 |
| WO | 03/063925 A1 | 8/2003 |
| WO | 2005/051170 A2 | 6/2005 |
| WO | 2005/078424 A1 | 8/2005 |
| WO | 2007/067743 A2 | 6/2007 |
| WO | 2008/141241 A1 | 11/2008 |
| WO | 2010/118335 A1 | 10/2010 |
| WO | 2010/123972 A1 | 10/2010 |
| WO | 2011/097586 A1 | 8/2011 |
| WO | 2011/101626 A1 | 8/2011 |

OTHER PUBLICATIONS

Brian Woodward et al., "The Sustainable Importance of Platinum in Biomedical Applications," MDDI Medical Device and Diagnostic Industry News Products and Suppliers (http://www.mddionline.com/print/7951), May 20, 2011, 9 pages.

* cited by examiner

| AVERAGE DATA FOR CORE PREP.: | | | | | |
|---|---|---|---|---|---|
| | I @ G0 | I @ G18 | % modulation | t90 (minutes) | absolute modulation | reflectance |
| AVERAGES: | 4802 | 8814 | 84 | 4 | 4011 | 210 |
| STD. DEVS.: | 394 | 622 | 7 | 0 | 327 | 22 |
| VARIANCE: | 8% | 7% | 8% | 8% | 8% | 10% |

| INDIVIDUAL CORE DATA: | | | | | | | |
|---|---|---|---|---|---|---|---|
| core # | I @ G0 | I @ G18 | % modulation | t90 (minutes) | absolute modulation | reflectance | |
| 227-145E | 4546 | 8331 | 83 | 3.4 | 3785 | 222 | 4 months storage at 4C, 0% RH |
| 227-145F | 5356 | 9436 | 76 | 4.0 | 4080 | 186 | |
| 227-145G | 4265 | 7661 | 80 | 3.1 | 3396 | 179 | |
| 227-145G | 4726 | 8675 | 84 | 4.0 | 3949 | 190 | |
| 227-145L | 4681 | 8910 | 90 | 3.5 | 4229 | 239 | 4 months storage at RT, 0% RH |
| 227-145M | 4487 | 8420 | 88 | 4 | 3933 | 209 | |
| 227-145N | 5401 | 9219 | 71 | 3.9 | 3819 | 208 | 4C, wet CTRL |
| 227-145O | 5151 | 9763 | 90 | 3.6 | 4612 | 245 | |
| 227-145P | 4463 | 8489 | 90 | 3.5 | 4026 | 198 | |
| 227-145Q | 4948 | 9232 | 87 | 3.6 | 4284 | 220 | |

FIG. 5

CRITICAL POINT DRYING OF HYDROGELS IN ANALYTE SENSORS

CROSS-REFERENCE TO RELATED APPLICATION

The present application claims the benefit of priority to U.S. Provisional Application Ser. No. 61/879,475, filed on Sep. 18, 2013, which is incorporated by reference in its entirety.

FIELD OF THE INVENTION

The invention relates to critical point drying ("CPD") and, more particularly, to CPD of a hydrogel-based device such as, for example and without limitation, a sensor platform of an analyte sensor (e.g., an optical-based or electrochemical analyte sensor) that uses a polymer-indicator system that is based on hydrogels. CPD allows for a hydrogel to be kept in its hydrated state and improves longevity and shelf life of the sensor and further allows the sensor to be implanted into a patient without re-hydrating the sensor. CPD dehydrates the hydrogel without leaving it vulnerable to cracking or disrupting its structure, and thus ensures proper sensor operation after implantation.

BACKGROUND

An exemplary analyte sensor 10 with which aspects of the invention may be employed is shown in FIG. 1. The sensor may be implantable subcutaneously or in the intraperitoneal fluid and is configured for detecting an analyte of interest, such as glucose. The sensor 10 includes a sensor body 12, a matrix layer (or indicator) 14 coated over part or all of the exterior surface of the sensor body 12, with fluorescent indicator molecules 16 distributed throughout the layer, a light source 18, e.g. an LED, that emits light, including light over a range of wavelengths which interact with the indicator molecules (referred to herein simply as "light at a wavelength which interacts with the indicator molecules"), i.e., in the case of a fluorescence-based sensor, a wavelength which causes the indicator molecules 16 to fluoresce, and a photosensitive element 20, e.g. a photodetector, which, in the case of a fluorescence-based sensor, is sensitive to fluorescent light emitted by the indicator molecules 16 such that a signal is generated in response thereto that is indicative of the level of fluorescence of the indicator molecules.

In some embodiments the indicator molecules are contained within the matrix layer 14, which comprises a biocompatible polymer matrix that is prepared according to methods known in the art and coated on the surface of the sensor body. Suitable biocompatible matrix materials, which must be permeable to the analyte, include hydrogels which, advantageously, can be made selectively permeable—particularly to the analyte—i.e., they perform a molecular weight cut-off function. The sensor 10 may also include reflective coatings 32 formed on the ends of the sensor body 12, between the exterior surface of the sensor body and the matrix layer 14, to maximize or enhance the internal reflection of the light and/or light emitted by fluorescent indicator molecules.

The sensor 10 may be configured to be implantable in a patient and may be constructed in such a way that no electrical leads extend into or out of the sensor body to supply power to the sensor (e.g., for driving the source 18) or to transmit signals from the sensor. Thus, the sensor may include a means for receiving power from an external source 40 that is wholly embedded or encapsulated within the sensor body 12 and a transmitter 42 that also is entirely embedded or encapsulated within the sensor body 12.

As still further illustrated in FIG. 1, an optical filter 34 may be provided on the light-sensitive surface of the photosensitive element (photodetector) 20. This filter prevents or substantially reduces the amount of light generated by the source 18 from impinging on the photosensitive surface of the photosensitive element 20. At the same time, the filter allows fluorescent light emitted by fluorescent indicator molecules 16 to pass through it to strike the photosensitive region of the detector. In addition, a temperature sensor 64 and an optional signal amplifier 66 may also be provided. The temperature sensor 64 measures the locally surrounding temperature of the ambient tissues and the indicator molecule environment and provides this information to the control logic circuit (not shown). The control logic circuit correlates fluorescence level, for example, with analyte concentration level, thereby correcting the output signal for variations affected by temperature. Amplifier 66 is a relatively simple gain circuit which amplifies the signal generated by the photodetector 20.

The various components and circuitry of the sensor 10 may be assembled onto a ceramic (e.g., ferrite) substrate 70.

Exemplary sensors are described in U.S. Pat. Nos. 5,517,313; 6,330,464; and 6,400,974, as well as in U.S. patent application Ser. No. 13/761,839, the respective disclosures of which are hereby incorporated by reference in their entireties.

If a sensor is implanted in the body of a living animal, the animal's immune system may begin to attack the sensor. For instance, if a sensor is implanted in a human, white blood cells attack the sensor as a foreign body, and, in the initial immune system onslaught, neutrophils are the primary white blood cells attacking the sensor. The defense mechanism of neutrophils includes the release of highly caustic substances known as reactive oxygen species. The reactive oxygen species include hydrogen peroxide.

In some non-limiting embodiments, the indicator 14 may be covered by a thin layer (e.g., 10 nm) on the outside of the indicator. The thin layer may protect against indicator molecule degradation. The thin layer may be platinum, and the platinum may be sputtered onto the outside surface of the indicator. Platinum rapidly catalyzes the conversion of hydrogen peroxide into water and oxygen, which are harmless to the sensor. The rate of this reaction is much faster than the boronate oxidation; thus, the platinum provides some protection against oxidation by reactive oxygen species. Although platinum is the catalyst of the conversion of hydrogen peroxide into water and oxygen in some embodiments, in alternative embodiments, other catalysts of this reaction, such as, for example, palladium or catalase, may be used for the thin layer instead of or in addition to platinum.

Under certain circumstances, after a sensor is assembled, it may be washed and then air dried (e.g., using heat, ambient air, dry gases or gases of a controlled humidity). When heat dried or air/gas dried, however, the hydrogel tends to shrivel like a dry sponge. This shriveling can cause a sputtered protective catalyst (such as platinum) to crack as the sensor is drying, which may pose a problem when the sensor is rehydrated and implanted. Cracking of protective catalyst may leave areas of the sensor vulnerable to attack by the immune system.

In addition to the physical damage (surface morphology) to the indicator or platinum layer due to shrinkage and cracking that accompanies air drying, another challenge involves long hydration periods that are required prior to implanting an air-dried sensor—especially after a period of storage. For air dried sensors, the average hydration period, or time to reach equilibration of in vivo signal, ranges from 30 minutes to 7 days depending on the storage time of the hydrogel (FIG. 2). This inconsistent behavior makes it difficult to predict the hydration profile of the hydrogel and time to stable baseline signal once inserted into a patient. Also, longer storage times in the dried state may cause irreversible signal loss that can never be regained due to the instability of the hydrogel in its unhydrated state (FIG. 2).

In the example shown in FIG. 2, the expected rehydration point of the hydrogel is shown to reach approximately 6 on the normalized signal scale. As can be seen in the plot, the signals of sensors that have been stored for 4 weeks reach the expected normalized signal level within a few days. Sensors stored for 8 weeks eventually reach the expected normalized signal level of 6, but it takes 5-6 days to reach that level. On the other hand, the signal level of sensor stored for 4 months or more never reach the expected normalized signal level.

Thus, as shown in FIG. 2, as the hydrogel is stored for periods greater than one month, the hydration of the hydrogel may take days or even months to equilibrate. Storage longer than 4 months does not allow the hydrogel to rehydrate at all.

Thus, a need exists for techniques for improving the longevity (shelf life) and rehydration characteristics of hydrogels employed in analyte sensors while minimizing or eliminating the surface morphology associated with air drying.

SUMMARY OF THE INVENTION

Critical point drying ("CPD") preserves the structure of specimen which could otherwise be damaged due to surface tension when changing from a liquid state to a gaseous state. In one embodiment, a CPD technique dehydrates the hydrogel of a hydrogel-based device (e.g., a sensor) without altering the surface or bulk morphology of the gel. The hydrogel is thus less vulnerable to collapsing, rearranging, or disrupting its structure. The hydrogel-based device can be dried easily in a critical point dryer since liquid $CO_2$ used in the CPD process, for example, changes from the liquid phase to the gas phase instantaneously without affecting the sensor gel morphology. An unaffected sensor morphology ensures proper hydrogel-based device operation after implantation.

Critical point drying is extremely useful for dehydrating, while maintaining the structure of the hydrogel. At a specific and fixed temperature, it has been found that the percent modulation, absolute modulation, and the reflection of the sensors remains at a high percentage.

CPD produces a gel with substantially unaltered structure/morphology, yields a faster hydration time, and allows a hydrogel-based device to be stored for an extended period (weeks and months) without degradation of the indicator molecule(s). In addition CPD is especially useful for drying without collapsing or deforming the structure of wet, fragile specimens (e.g., sensor hydrogel).

One aspect of the invention may provide a method of preparing a hydrogel for a hydrogel-based device. The method may comprise drying the hydrogel by a critical point drying technique.

In some embodiments, the hydrogel-based device comprises a sensor configured for sensing the presence of an analyte in contact with the sensor. The sensor may include an indicator comprising the hydrogel and configured to emit a detectable signal or a change in a detectable signal indicating the presence of the analyte.

In some embodiments, the critical point drying technique may comprise: replacing water within the hydrogel with an intermediate fluid that is miscible with water and $CO_2$. The critical point drying technique may comprise replacing the intermediate fluid within the hydrogel with $CO_2$. The critical point drying technique may comprise manipulating temperature and pressure to achieve super critical $CO_2$. The critical point drying technique may comprise removing the supercritical $CO_2$ from the hydrogel. In some embodiments, the temperature for achieving super critical $CO_2$ may be, preferably, about 30-35° C. and the pressure for achieving supercritical $CO_2$ may be, preferably, about 1000-1200 psi.

In some embodiments, the method may further comprise storing the hydrogel-based device at room temperature after the critical point drying step. In some embodiments, the method may further comprise implanting the hydrogel-based device into a patient after the critical point drying step without pre-hydrating the hydrogel-based device prior to implanting.

Another aspect of the invention may provide a hydrogel dried by a critical point drying technique.

In some embodiments, the critical point drying technique may maintain the physical properties of the hydrogel. In some embodiments, the critical point drying technique may extend the shelf life of the hydrogel. In some embodiments, the critical point drying technique may not change the performance of the hydrogel in one or more of in vitro and in vivo environments.

Still another aspect of the invention may comprise a sensor configured for sensing the presence of an analyte in contact with the sensor. The sensor may comprise an indicator configured to emit a detectable signal or a change in a detectable signal indicating the presence of the analyte. The indicator may comprise a hydrogel dried by a critical point drying technique.

Further variations encompassed within the devices, systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 5 is a table showing glucose response data obtained on a fluorometer for a number of sensors dried by a critical point drying technique having been stored for four months at different conditions.

DETAILED DESCRIPTION OF THE INVENTION

Figure 1:
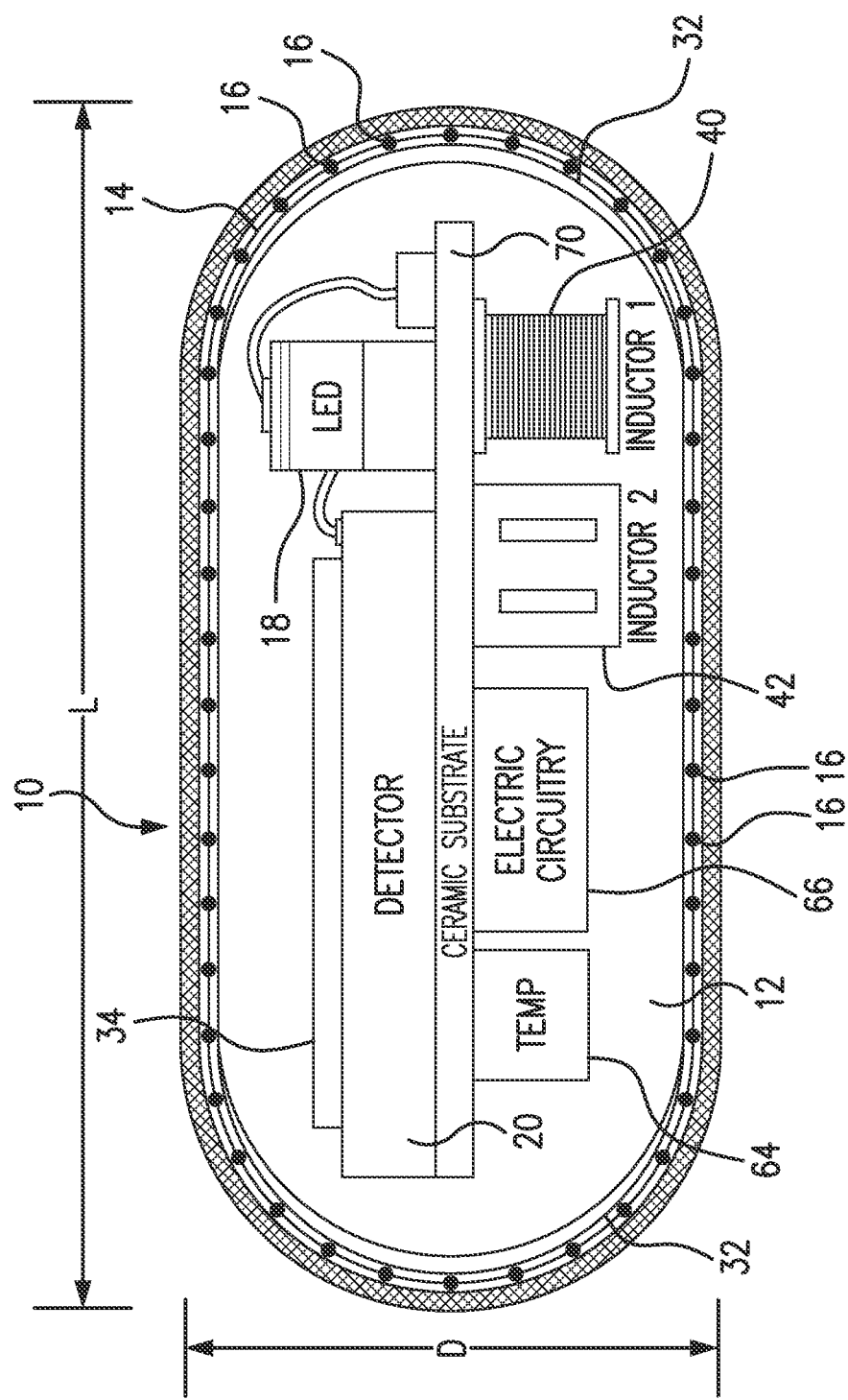
FIG. 1 is a schematic view of an exemplary analyte sensor incorporating indicator molecules suspended in a hydrogel.

Unless defined otherwise, all terms of art, notations and other scientific terms or terminology used herein have the same meaning as is commonly understood by one of ordinary skill in the art to which this disclosure belongs. All patents, applications, published applications, and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, inside, outside, inner, outer, proximal, distal, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Critical point drying of specimens has been used to process samples for scanning electron microscopy imaging ("SEM"). The process is most useful for understanding how a specimen looks like in an in vivo environment, such as tissue or muscle, because it allows the sample to remain in the hydrated state when no water or liquid is present, which is necessary for samples in an SEM.

Figure 3:
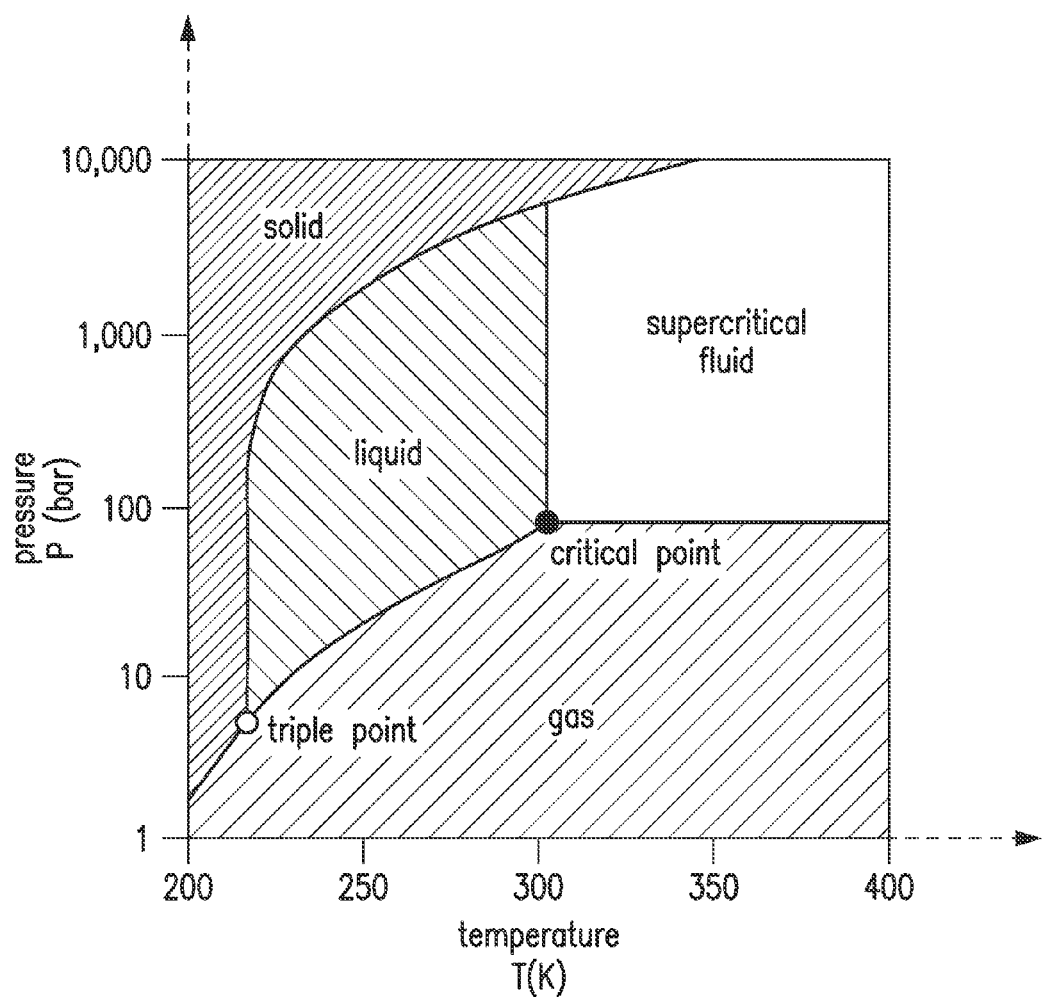
FIG. 3 is a pressure versus temperature plot showing different phases and the critical point for carbon dioxide $CO_2$.

The phase diagram (FIG. 3) shows the pressure to temperature ranges where solid, liquid and vapor exist. The boundaries between the phases meet at a point on the graph called the triple point. Along the boundary between the liquid and vapor phases, it is possible to choose a particular temperature and corresponding pressure in which liquid and vapor can co-exist (i.e., have the same density). This is known as the critical temperature and pressure.

Critical point drying relies on this physical principle. The water in the material is replaced with a suitable inert fluid whose critical temperature for a realizable pressure is just above ambient. The choice of fluids is severely limited (for example, the critical point of water is about 374° C. and 3212 psi, making it an impractical fluid for CPD), and therefore, $CO_2$ is the fluid that is often used. With $CO_2$, a critical point of, preferably, approximately 30-35° C. can be achieved at a pressure of, preferably, around 1000-1200 psi. Therefore, if the water is replaced with liquid $CO_2$ and the temperature is then raised above the critical temperature, the liquid $CO_2$ changes to vapor without change of density and therefore without surface tension effects which can distort the structure of the material. Since liquid $CO_2$ is not sufficiently miscible with water, however, it may be useful to use an intermediate fluid which is miscible with both water and liquid $CO_2$. In one embodiment of the CPD process, the intermediate fluid used is methanol. In another embodiment, the intermediate fluid is ethanol or acetone.

Thus, CPD involves the rapid transformation of liquid into gas via conversion of liquid into a supercritical fluid. This process is achieved by bringing the liquid to its critical point (FIG. 3), via manipulation of the temperature and pressure, which allows the liquid to skip the phase boundaries between the liquid and gas phases and instantly become gas, leaving the material dry but locked into its "hydrated" state, i.e., without the surface damage and other morphology due to surface tension that accompanies phase transitions during air drying.

This procedure is achieved by replacing water with a liquid that is both miscible with water and liquid $CO_2$, such as methanol, ethanol, acetone, or isopropanol, termed the intermediate fluid. In an exemplary, non-limiting implementation, the material is taken through a series of intermediate fluid exchanges that slowly replace the water with the miscible liquid until the specimen is completely immersed in 100% intermediate fluid. The specimen then goes through a second series of fluid exchanges that replace the miscible intermediate fluid with liquid $CO_2$, and then the temperature and pressure are manipulated in order to create supercritical $CO_2$ that can instantly be converted to gaseous $CO_2$ leaving the "hydrated" structure in place.

Critical point drying allows a hydrogel to be stored in a hydrated state, which maintains its physical properties, increases its shelf life, and also eliminates the necessity for a pre-hydration step prior to implant into patients. The CPD process locks the hydrogel in the hydrated state by the instantaneous removal of the supercritical $CO_2$ via pressure and temperature manipulation forcing the liquid into the gas phase and leaving the hydrogel in its hydrated or expanded state. Examples of some hydrogels that may be dried by a critical point drying technique and/or used in analyte sensing include, but are not limited to, poly(HEMA), poly(vinyl alcohol), poly(ethylene glycol), silicone, acrylamides and copolymers, and natural hydrogel materials (e.g., agarose, methylcellulose, hyaluronan).

Figure 2:
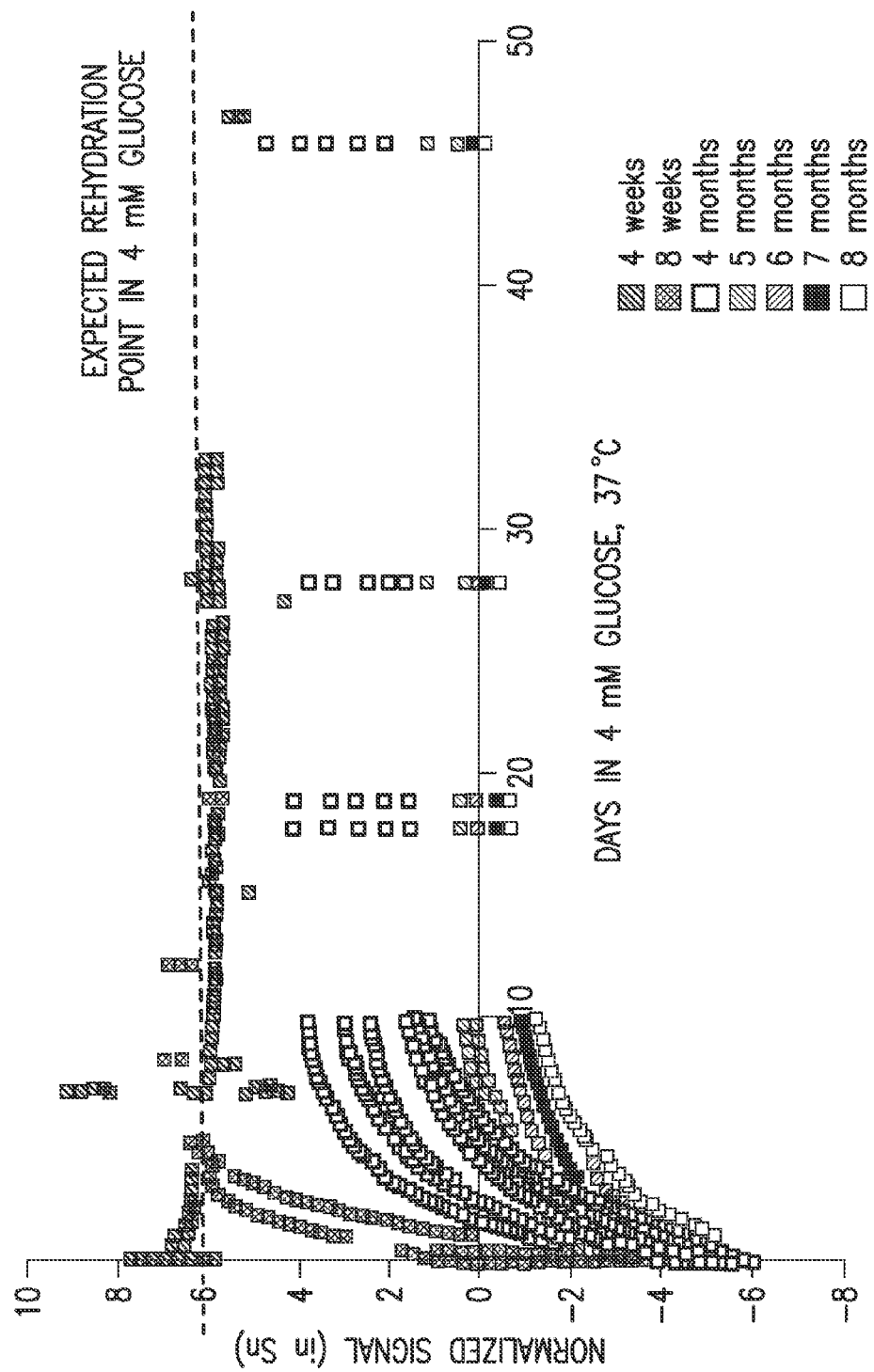
FIG. 2 is a plot of signal strength versus number of days exposed to glucose for different analyte sensors having been air dried and stored for various periods of time.
Figure 4:
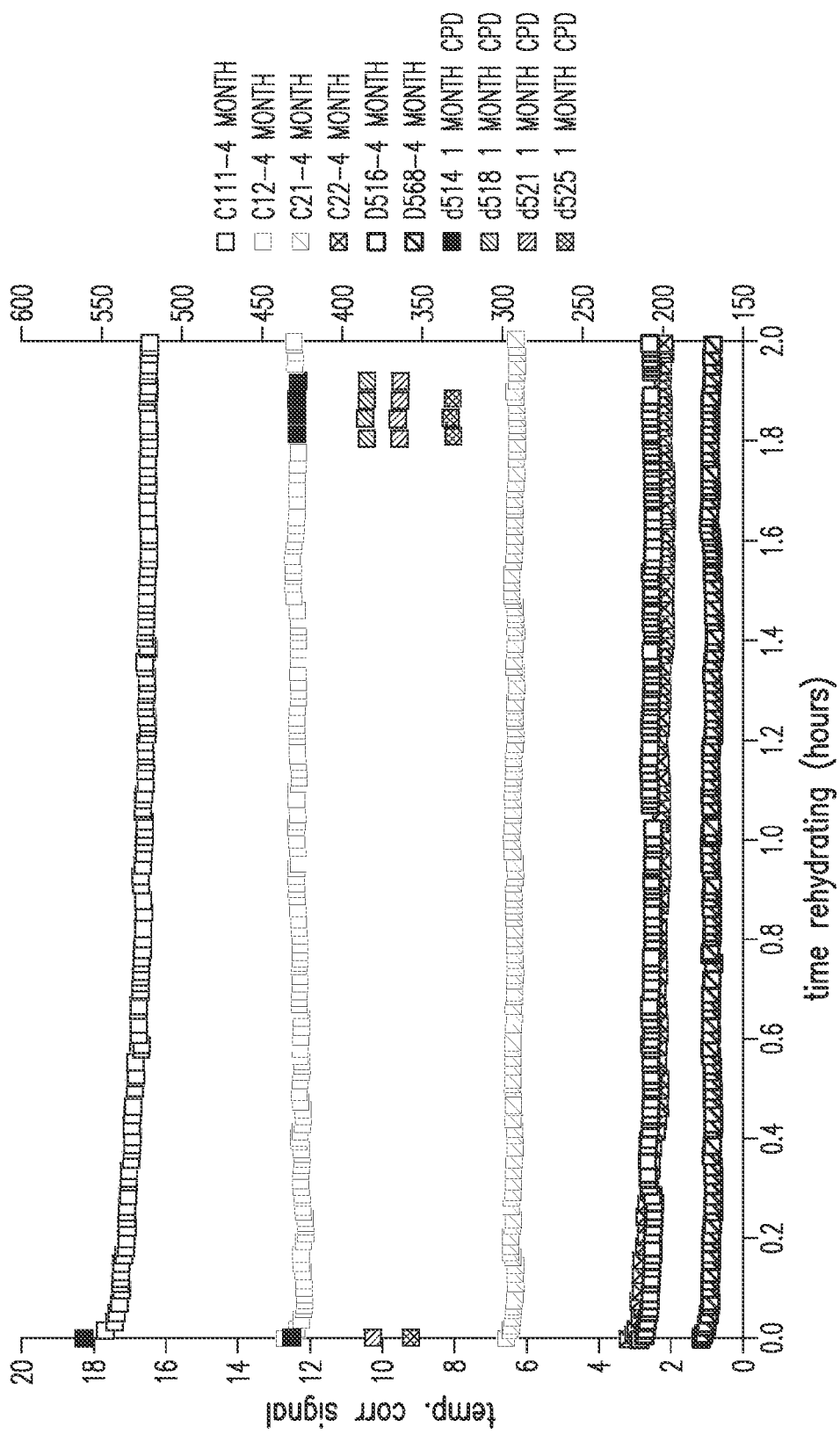
FIG. 4 is a plot of signal versus time exposed to rehydrating fluid for a number of analyte sensors dried by a critical point drying technique and stored for four months or one month.

As explained above and illustrated in FIG. 2, upon insertion into solution, hydrogel-based devices (e.g., sensors) having air-dried hydrogel take long periods of time to reach equilibrium, depending on how long the hydrogel is stored dry. In one illustrative example, as the hydrogel sits dry, the useful shelf-life may become undeterminable past 8 weeks, and at 8 weeks it takes approximately 5 to 6 days for the hydrogel to equilibrate to its pre-dried signal. FIG. 4 shows sensors that were processed by CPD techniques and stored for various amounts of time followed by monitoring rehydration of the critical point dried hydrogel. The baseline signal reaches a plateau for all sensors stored at 1 and 4 months within 20 minutes and the signal variation during the initial stabilization period is less than 5% of the baseline signal, meaning that the hydrogel is "hydrated" and potentially ready for in vivo use immediately.

The fluorescent response to glucose of the CPD hydrogel were monitored as a function of storage time and showed no loss of those critical parameters such as baseline fluorescence ($I_0$), % modulation, absolute modulation, T90 and reflectance compared to controls which were never dried (FIG. 5). In these non-limiting examples, the critical point dried samples (cores) maintained their high performance even when they were stored for 4 months at room temperature. This advantageous ability to operate at room temperature improves storage and handling of the final device.

There are advantages (for example, such as those described herein) to utilizing the CPD process which allows for the long-term storage (e.g. approximately 6 months) of hydrogel-based sensor platforms as well as the ability to maintain both the baseline and modulatable signal. The process also allows for the sensor to be implanted without a pre-hydration period—typically a minimum of 6 hours in sterile saline solution—to allow the air-dried hydrogel to reach some form of hydration prior to implantation.

Figure 6:
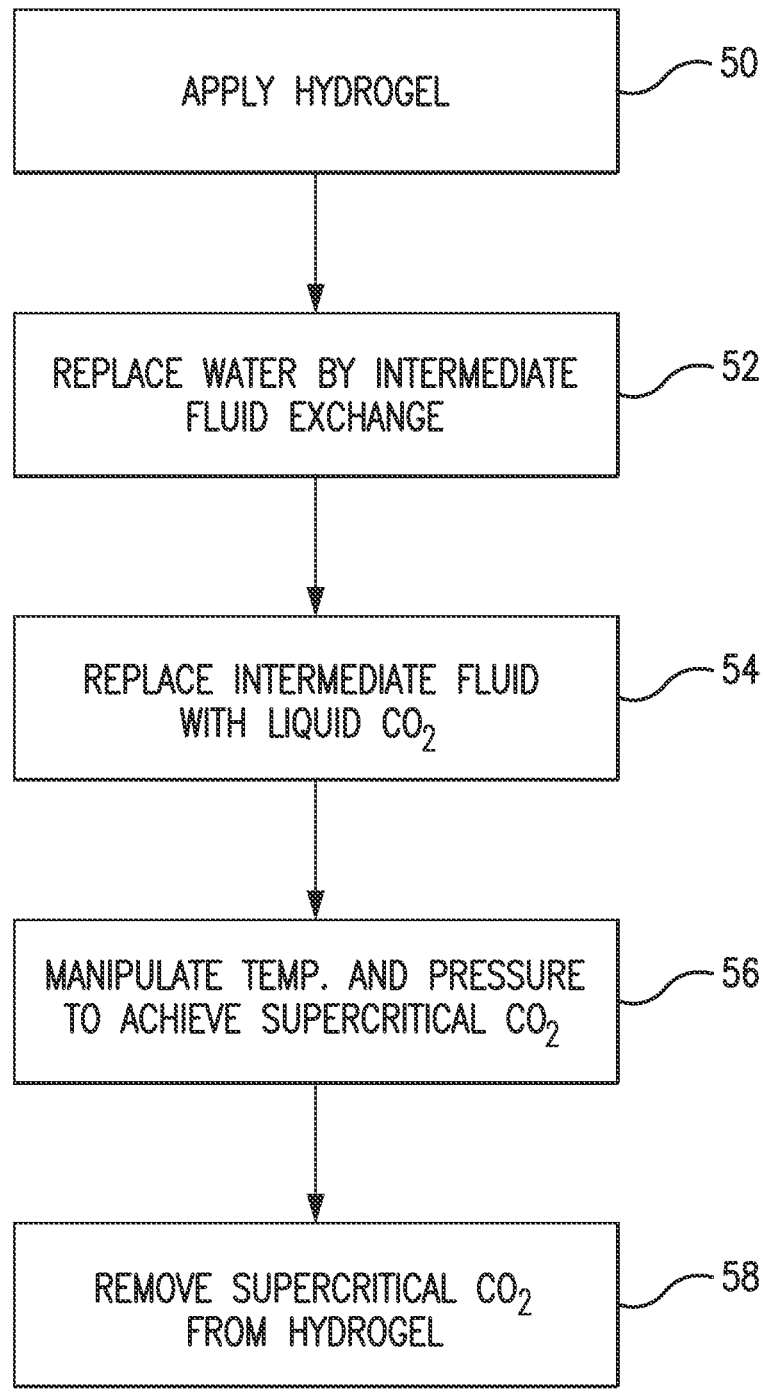
FIG. 6 is a flow chart illustrating a critical point drying technique for preparing an analyte sensor with a hydrogel indicator in accordance with one embodiment of the present invention.

An exemplary method for employing a CPD technique for drying a hydrogel of an analyte sensor is shown in FIG. 6. In step 50, a hydrogel is applied to all or part of the surface of a sensor housing. Step 50 may or may not be the final step in fabricating the sensor. After step 50, when fabrication of the sensor is complete, or the sensor is otherwise ready to be dried, in step 52, water in the hydrogel is replaced with a liquid that is miscible with both water and liquid $CO_2$, such as an intermediate fluid such as methanol, ethanol, acetone, or isopropanol, in an intermediate fluid exchange step. Step 52 is performed by taking the material through a series of intermediate fluid exchanges that slowly replace the water with the miscible liquid (intermediate fluid) until the specimen is completely immersed in 100% intermediate fluid. In step 54, the hydrogel goes through a second series of fluid exchanges that replace the miscible intermediate fluid with liquid $CO_2$. After the intermediate fluid is replaced by the liquid $CO_2$, in step 56, the temperature and pressure of the hydrogel are manipulated to create supercritical $CO_2$ that can instantly be converted to gaseous $CO_2$. In step 58, the gaseous $CO_2$ is removed from the hydrogel, leaving the hydrated structure of the hydrogel in place.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although some embodiments described above relate to critical point drying of hydrogels for use as an analyte indicator of an analyte sensor, the present invention is not limited to critical point drying of hydrogels in the analyte sensor environment. Some alternative embodiments relate to critical point drying of hydrogels for use in other hydrogel-based devices and/or other environments, such as, for example and without limitation, hydrogels for use as scaffolds in tissue engineering, hydrogels for use as sustained-release drug delivery systems, and hydrogels for use in implantable and non-implantable medical devices.

The invention claimed is:

1. A method of preparing a hydrogel for a hydrogel-based analyte sensor configured for sensing the presence of an analyte in contact with the analyte sensor, the method comprising:
  applying the hydrogel to all or part of a surface of a sensor housing of the analyte sensor, wherein the hydrogel comprises indicator molecules that are configured to emit a detectable signal or a change in a detectable signal indicating the presence of the analyte;
  applying a protective catalyst to the hydrogel, wherein applying the protective catalyst to the hydrogel comprises sputtering the protective catalyst on the hydrogel; and
  drying the hydrogel, which (i) comprises the indicator molecules, (ii) has been applied to all or part of the surface of the sensor housing, and (iii) to which the protective catalyst has been applied, by a critical point drying technique that comprises:
    replacing water within the hydrogel with an intermediate fluid that is miscible with water and $CO_2$;
    replacing the intermediate fluid within the hydrogel with $CO_2$;
    manipulating temperature and pressure to achieve super critical $CO_2$; and
    removing the supercritical $CO_2$ from the hydrogel.

2. The method of claim 1, wherein the temperature for achieving super critical $CO_2$ is about 30-35° C., and the pressure for achieving supercritical $CO_2$ is about 1000-1200 psi.

3. The method of claim 1, further comprising storing the hydrogel-based analyte sensor at room temperature after the critical point drying step.

4. The method of claim 1, further comprising implanting the critical point dried hydrogel-based analyte sensor into a living being without pre-hydrating the hydrogel-based analyte sensor prior to implanting.

5. The method of claim 1, wherein the protective catalyst is platinum.

* * * * *